United States Patent [19]

Schoerner et al.

[11] Patent Number: 5,140,275

[45] Date of Patent: Aug. 18, 1992

[54] METHOD AND APPARATUS FOR MEASURING THE AMOUNT OF ICE IN AN AQUEOUS ICE SLURRY

[75] Inventors: William S. Schoerner, Plainfield, Ill.; Tushar K. Shah, Houston, Tex.

[73] Assignee: Chicago Bridge & Iron Technical Services Company, Oak Brook, Ill.

[21] Appl. No.: 596,370

[22] Filed: Oct. 12, 1990

[51] Int. Cl.$^5$ ............................................. G01N 27/04
[52] U.S. Cl. ..................................... 324/693; 73/61.43
[58] Field of Search ............... 73/61 R; 324/693, 694, 324/691; 62/125, 127, 129, 130

[56] References Cited

U.S. PATENT DOCUMENTS

| | | | |
|---|---|---|---|
| 4,286,436 | 9/1981 | Engdahl et al. | 62/123 |
| 4,838,039 | 6/1989 | Knodel | 62/330 |
| 4,850,202 | 7/1989 | Kito et al. | 73/61 R X |

FOREIGN PATENT DOCUMENTS 297547  11/1989  Japan ...................................... 324/693

Primary Examiner—Hezron E. Williams
Assistant Examiner—Joseph W. Roskos
Attorney, Agent, or Firm—Marshall, O'Toole, Gerstein, Murray & Bicknell

[57] ABSTRACT

The ice content of a mixture of ice and liquid water is determined by (a) measuring the electrical conductivity $C_i$ of the original water at a temperature above its freezing point and before any of it has been converted to ice; (b) cooling the water to produce a mixture of ice and a liquid water phase; (c) measuring the electrical conductivity $C_n$ of the liquid water phase; and (d) computing the fraction of ice in the mixture by use of the equation $$F = 1 - C_i/C_n$$

wherein F is the fraction of ice in the mixture, $C_i$ is the electrical conductivity of the original water before ice formation therein, and $C_n$ is the electrical conductivity of the liquid water phase in the mixture having the ice fraction F.

19 Claims, 3 Drawing Sheets

METHOD AND APPARATUS FOR MEASURING THE AMOUNT OF ICE IN AN AQUEOUS ICE SLURRY

The present invention relates to a method and apparatus for measuring the quantity or amount of ice produced by cooling water until ice forms.

BACKGROUND OF THE INVENTION

It is sometimes important to be able to measure the amount of ice which results from cooling water to its freezing point. For this purpose, various types of sophisticated sonar, mass flow and radiation devices have been employed. These devices are not only expensive and complicated but of questionable reliability. The present invention fills a need by providing a simple method and inexpensive apparatus which can be used to determine the amount of ice produced by cooling water until it freezes, particularly with the ice in admixture with the liquid water phase, and especially as an ice slurry.

BRIEF DESCRIPTION OF THE INVENTION

In accordance with the invention, the amount of ice produced from water containing dissolved minerals is determined by measuring the electrical conductivity of the liquid water phase mixed with the ice and comparing the conductivity of the liquid water phase with the conductivity of the original water.

The invention is based on the principle that the concentration of dissolved minerals present as ions in the liquid water phase increases as the water is cooled to cause the formation of ice. This result follows from the fact that the ice which is formed consists of essentially pure water containing no minerals. Accordingly, the dissolved ionic minerals present in the original water concentrate in the residual liquid water phase as more and more of the water is converted to ice. Furthermore, as the concentration of dissolved ionic minerals in water increases, the electrical conductivity of the water increases. Chemically pure water is a very poor conductor of electricity, but water having dissolved minerals which produce ions therein, e.g., the minerals typically dissolved in tap water, has an increased electrical conductivity which is essentially proportional to the concentration of the dissolved ions, a relationship which is clearly applicable to water containing up to about 2,000 ppm of dissolved ionic minerals.

The invention thus provides a method of determining the electrical conductivity of water containing a measured concentration of dissolved minerals by cooling at least some of the water to form ice in a liquid water phase; measuring the increase in the electrical conductivity of the liquid water phase due to the increase in the mineral content thereof as a result of the natural exclusion of minerals from the ice; and correlating the measured electrical conductivity of the water to the liquid water phase not converted to ice to determine the amount of ice which has been produced.

The invention also includes the method of isolating a mass of water containing a measured concentration of dissolved minerals; determining the electrical conductivity of the undiluted unconcentrated water; cooling increasing amounts of the mass of water to form ice, in a progressively increasing amount, in a liquid water phase; measuring the increase in the electrical conductivity of the cool water due to the progressive increase in the mineral content of the liquid water phase as a result of the natural exclusion of minerals from the ice; and correlating the measured electrical conductivity of the water before any of the water is converted to ice, to the electrical conductivity of the liquid water phase not converted to ice to determine the amount of ice which has been produced.

More specifically, the invention provides a method of determining the amount of ice slurry in an ice storage tank which comprises firstly determining the electrical conductivity of water containing a measured amount of dissolved minerals; feeding a volume of the water, some of which may be in the form of ice, to an ice storage tank; cooling increasing amounts of the tank water to form more ice and storing the additional ice in the tank; secondly determining the increase in the electrical conductivity of the liquid water phase in the tank due to the natural progressive increase in the mineral content of the water as the amount of water in liquid phase decreases and the amount of ice increases; and by means of the difference between the first and second electrical conductivities determining the portions of ice and water in liquid phase in the tank.

Also provided by the invention is a method of determining the portions of ice and water in a storage tank in which the ice in the storage tank is produced by freezing a portion of a known volume of water having a dissolved mineral content of measured amount when the water is entirely in the liquid phase; the volume of water in liquid phase, before any ice is produced from it, having an initial electrical conductivity; the tank also containing essentially all of the remaining portion of the volume of water in liquid phase; said ice portion being formed with essentially all of the dissolved mineral content being excluded from the ice and remaining dissolved in the liquid water phase portion, so that by measuring the electrical conductivity of the remaining portion of the volume of water in liquid phase and comparing its measured electrical conductivity with the measured electrical conductivity of the water volume before any of the water volume is converted to ice and, by means of the difference between the two electrical conductivities, determining the portions of ice and water in liquid phase in the tank.

Desirably, before any portion of the water is frozen to ice, it has a maximum dissolved mineral content of about 2000 ppm.

The ice can be formed in the storage tank. However, the ice can also be formed outside of the tank using water withdrawn from the water volume in the tank, and the resulting ice admixed with water subsequently fed to the tank interior.

More specifically the invention provides a method of (a) measuring the electrical conductivity $C_i$ of water at a temperature above its freezing point; (b) cooling the water to produce a mixture of ice and a liquid water phase; (c) measuring the electrical conductivity $C_n$ of said liquid water phase; and (d) computing the fraction of ice in said mixture by use of the equation $$F = 1 - C_i/C_n \qquad (A)$$

wherein F is the fraction of ice in the mixture, $C_i$ is the conductivity of said water before ice formation therein, and $C_n$ is the conductivity of said liquid water phase in a mixture having the ice fraction F.

Furthermore, the amount of ice in an ice slurry comprising a mixture of ice and a liquid water phase containing dissolved minerals can be determined by (a) measuring the electrical conductivity of the liquid water phase of the ice slurry; (b) isolating a representative sample of the ice slurry; (c) heating the ice slurry sample to melt all of the ice therein; (d) measuring the electrical conductivity of the melted ice slurry sample; and (e) calculating the ice fraction by use of the equation:

$$F = 1 - C_i/C_n$$

wherein F is the fraction of ice in the ice slurry, $C_i$ is the conductivity of the melted ice slurry sample, and $C_n$ is the conductivity of said liquid water phase of the ice slurry having the ice fraction F.

Additionally provided is a method for the continuous measurement of an ice fraction in an ice slurry, comprising a mixture of ice and a liquid water phase containing dissolved minerals, passing a given point, said method comprising the steps of (a) measuring the conductivity $C_n$ of the liquid water phase of the ice slurry at said point; (b) isolating a representative sample of the ice slurry; (c) heating said sample sufficiently to melt all of the ice therein; (d) measuring the conductivity $C_i$ of said melted ice slurry sample; and (e) calculating the ice fraction by use of the equation $$F = 1 - C_i/C_n \quad (A)$$

wherein F is the fraction of ice in the ice slurry, $C_i$ is the conductivity of said melted ice slurry sample, and $C_n$ is the conductivity of said liquid water phase of the ice slurry having the ice fraction F.

Equation (A) above used for computing the fraction of ice produced on freezing water can be derived as follows using the following nomenclature:

M = weight of water in the system.
S = weight of dissolved ionic materials in the system.
I = weight of ice produced.
$C_i$ = initial concentration of dissolved ionic materials before production of any ice.
$C_n$ = concentration of dissolved ionic compounds after production of ice in the amount I.

If it is also assumed that all of the dissolved ionic minerals originally present in the water remain in solution, i.e., that none of these minerals precipitates out of solution, the initial concentration can be represented by
$$C_i = S/M \quad (1)$$

After the water has been cooled sufficiently to produce a weight of ice I, the resulting concentration of dissolved ionic minerals is
$$C_n = S/(M-I) \quad (2)$$

Equation (1) can be rearranged to read
$$S = C_i M \quad (3)$$

Substituting equation (3) into equation (2), the following can be derived:
$$I/M = 1 - (C_i/C_n) \quad (4)$$

where I/M is the fraction of ice which has been produced in the system by freezing at least some of the water.

Thus, the fraction of ice (I/M) in the system can be expressed as a function of the ratio of the initial concentration of dissolved ionic minerals in the water to the final concentration of such minerals after a portion of the water has been frozen. Further, once $C_i$ has been established, it is a constant in equation (4), which can then be used to express continuously the fraction of ice in a mass or volume of water which is being frozen or thawed.

While the mathematical treatment set out above is based on the concentration of ionic minerals dissolved in the water, the ionic concentration can be measured by measuring the electrical conductivity of the water. It is particularly accurate for concentrations not exceeding about 2,000 ppm of dissolved ionic minerals. Thus, the relationship expressed in equation (4) is essentially correct if the electrical conductivities of the initial and final water fractions are substituted for $C_i$ and $C_n$, respectively.

For use in the invention, any conductivity meter designed for use with water and having a range reading between 0 and 2,000 microsiemens is appropriate.

According to another aspect of the invention apparatus is provided comprising a storage tank adapted to contain a volume of water, having a dissolved mineral content, which can be cooled and converted to ice in a practical amount of up to about 70% or above of the water; a conduit communicating with the bottom interior of the tank for withdrawing liquid water from the tank and returning it to the tank; and means for measuring the electrical conductivity of the liquid water phase flowing through said conduit to thereby determine the amount of ice, if any, in the tank.

Also provided by the invention is apparatus comprising a main conduit through which an ice slurry, produced by cooling water having a dissolved mineral content to form an ice phase and liquid water phase, can flow; means to measure the electrical conductivity of the liquid water phase content of the ice slurry in the main conduit; a branch conduit communicating with the main conduit for withdrawing an ice slurry sample therefrom and delivering it to a pot; heater means associated with the pot to melt the ice in the sample and produce a totally liquid water phase sample; and means to measure the electrical conductivity of the totally liquid water phase sample in the pot.

A constant temperature controller can be associated with the pot to maintain the totally liquid phase sample at a temperature slightly above freezing. Also, a conduit can communicate with the pot for withdrawing the totally liquid water phase sample from the pot and returning it to the main conduit for addition to ice slurry flowing therein.

Specifically provided is apparatus for measuring the fraction of ice in a slurry produced by freezing an aqueous liquid comprising a conductivity cell for measuring the conductivity of water, said cell being connected in series with a variable resistor across a source of constant voltage; a first amplifier receiving at its input a first signal representing the voltage drop across said conductivity cell and producing an output signal $V_a$ representing said first signal; a second amplifier receiving at its input a second signal representing the voltage drop across said variable resistor and producing an output signal $V_b$ representing said second signal; a differential amplifier having two inputs, to one of which said signal $V_a$ is applied and to the other of which said signal $V_b$ is applied, the amplifier producing an output signal representing the difference $(V_a - V_b)$ between said input signals; an analog divider having a first input to which said signal $(V_a - V_b)$ is applied, and a second input to which said signal $V_b$ is applied, said divider producing an output signal $V_o$ representing the fraction $$\frac{V_a - V_b}{V_b}$$

and $V_o$ also representing the fraction of ice in an ice slurry introduced into said conductivity cell. All of the amplifiers can have unity gain. Also, the first and second amplifiers can be isolation amplifiers.

BRIEF DESCRIPTION OF THE DRAWINGS

The invention will be further explained in the following detailed description taken in conjunction with the accompanying drawings, in which.

DETAILED DESCRIPTION OF THE DRAWINGS

Figure 1:
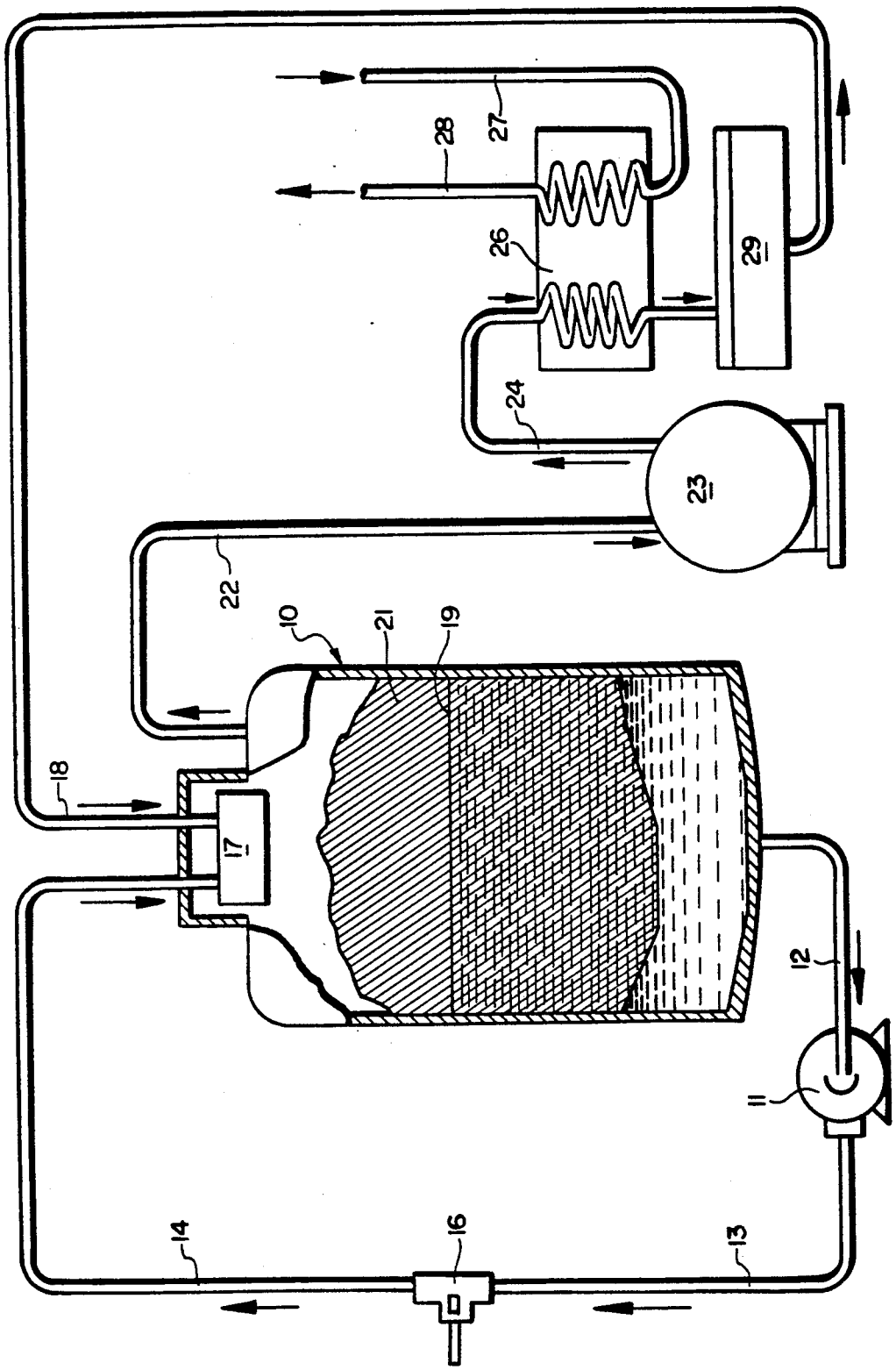
FIG. 1 is a schematic drawing of apparatus for measuring the fraction or portion of ice produced in situ in an ice storage vessel.

FIG. 1 illustrates the use of the invention in a direct freeze refrigeration storage system in which water is frozen by direct contact with a liquid refrigerant to produce ice crystals. The system shown in FIG. 1 includes an ice-storage tank 10 provided with a circulation pump 11 and appropriate conduits 12, 13 and 14 for recirculating liquid phase water from the bottom of the tank through an electrical conductivity meter 16, and back into the top interior of tank 10. At the top of tank 10, the stream of water entering through conduit 14 is mixed in freezer 17 with a stream of liquefied refrigerant gas, which is largely water insoluble. Some refrigerant gases which can be used are butane, isobutane, octafluorocyclobutane, a chloro and/or fluoro substituted derivative of methane or ethane, and especially dichlorotetrafluoroethane (a mixture of 1,2-dichloro-1,1,2,2-tetrafluoroethane and 1,1-dichloro-1,2,2,2-tetrafluoroethane, or a mixture of any of these refrigerants such as a mixture of dichlorotetrafluoroethane and dichlorodifluoromethane. The liquefied refrigerant gas is fed to freezer 17 by conduit 18. As a result of the contact between the stream of water and the refrigerant stream, the water is cooled and the liquefied refrigerant is converted to a gas, both of which enter tank 10. This method and apparatus for producing ice is disclosed in Knodel U.S. Pat. No. 4,838,039.

As the process proceeds, the recirculated water stream is cooled to its freezing point, causing a portion of the water to be converted to ice crystals which tend to accumulate on the surface 19 of the liquid water in tank 10. With further cooling, an increasing portion of the water in tank 10 is converted to ice and the vessel becomes filled with a porous mass 21 of ice crystals which resembles packed snow. Since the ice is porous and less dense than water, it tends to occupy a greater volume than the same water prior to freezing. In addition, as the water level in the ice mass falls, the ice loses some of its buoyancy and the ice becomes compacted under its own weight. For these reasons, it is often difficult to estimate the actual quantity of ice in the storage vessel, even when the top of the ice and/or the liquid level is known.

To properly monitor and control the refrigeration storage system shown in FIG. 1 during the freeze and subsequent melt cycles, it is important to be able to measure accurately the amount of ice which is produced. Such measurement is afforded in accordance with the invention by means of a conductivity meter or cell 16 which is installed in the recirculating system consisting of pump 11 and conduits 12, 13 and 14. As the amount of ice produced during the cooling cycle of the system increases, the conductivity of the water passing through the conductivity cell increases. At any time, therefore, the conductivity of the recirculating water can be measured and, with knowledge of the initial conductivity of the water before any ice is produced, the fraction of ice within the system can be determined by means of formula (4).

In ice storage tank 10, the refrigerant gas produced by contact with the incoming water in freezer 17 is drawn off through conduit 22 to the input of compressor 23. The compressed refrigerant gas passes through conduit 24 into heat exchanger 26 wherein it is cooled to its condensation point by suitable means, e.g., a countercurrent stream of cooling water entering through conduit 27 and leaving through conduit 28. The condensed refrigerant accumulates in receiver-separator 29 from which it is recycled to freezer 17 through conduit 18.

Figure 2:
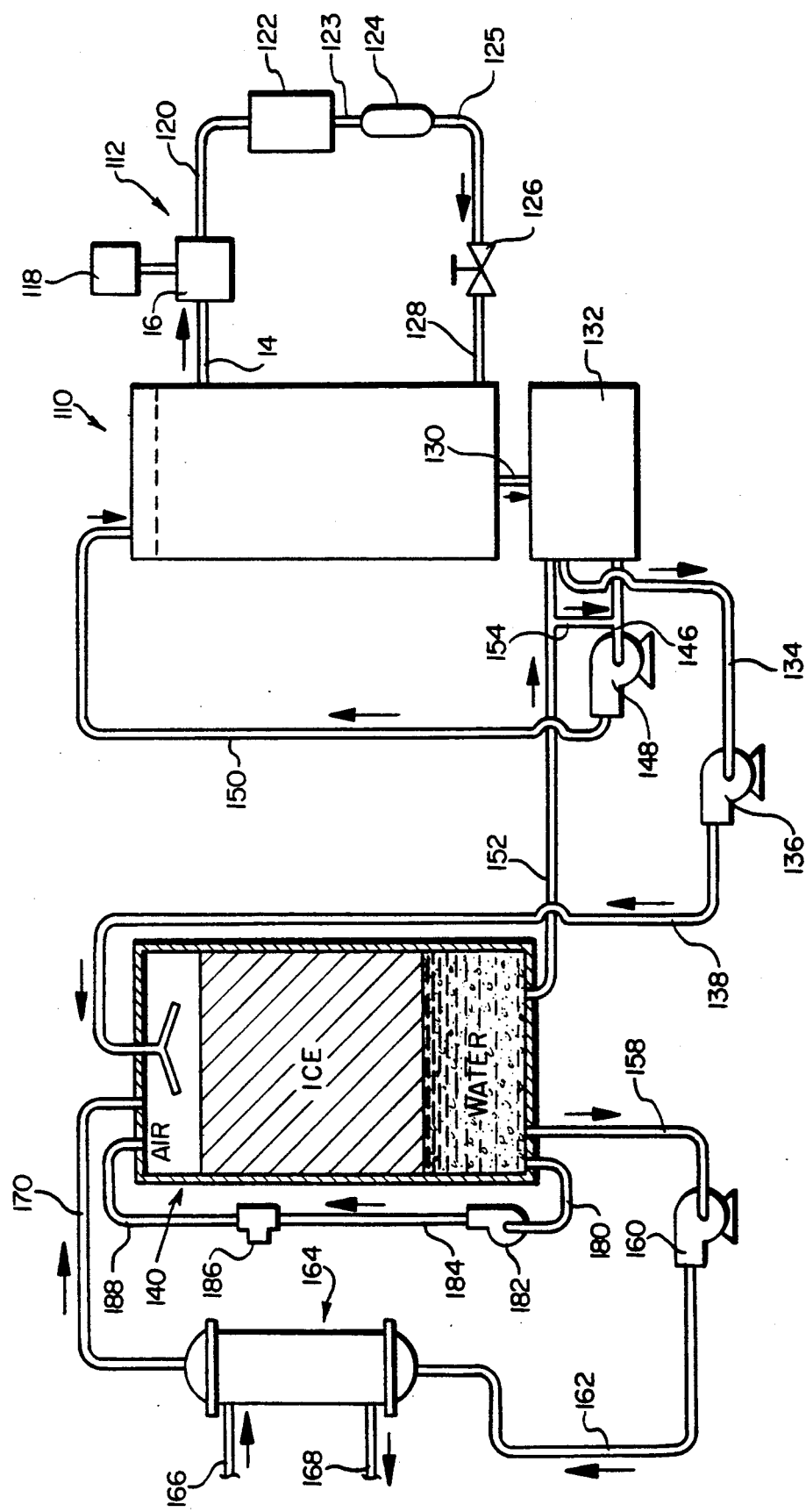
FIG. 2 is a schematic drawing of apparatus for measuring the fraction or portion of ice in an ice storage vessel in which the ice is formed outside of the tank.

With reference to FIG. 2 the freeze exchanger 110 is of the vertical shell and tube falling film type such as disclosed in U.S. Pat. No. 4,286,436. The shell side of the freeze exchanger 110 is cooled by means of a closed loop refrigeration system 112. Gaseous refrigerant, such as ammonia, is removed from the shell side of freeze exchanger 110 by conduit 114 and fed to compressor 116 driven by electric motor 118. The compressed refrigerant is fed from compressor 116 to conduit 120 which delivers it to condenser 122. The liquid refrigerant is removed, from condenser 122 by conduit 123 and delivered to refrigerant receiver 124 and then by conduit 125 to expansion valve 126 through which it is expanded to conduit 128 for delivery to the shell side of freeze exchanger 110.

Water is fed by conduit 150 to the top of freeze exchanger 110 and it flows as a thin falling film down the inner surface of the tubes. As the water flows downwardly in the tubes it is cooled and a portion of the water is converted to small ice crystals. The slurry mixture of water and ice flows from freeze exchanger 110 through outlet 130 to receiver tank 132.

The slurry is collected in receiving tank 132 and is withdrawn therefrom by conduit 134 and fed to pump 136 which delivers it to conduit 138 to be fed through the top to ice storage tank 140. Water in the lower part of receiving tank 132 is withdrawn by conduit 146 and fed to pump 148 which delivers it to conduit 150 for delivery to the top of freeze exchanger 110.

During ice building water is removed from ice storage tank 140 by means of conduit 152 and is fed to receiving tank 132 to be recycled through freeze exchanger 110. Alternatively, the water can be fed from conduit 152 to conduit 154 and then to conduit 146 which feeds it to pump 148 for recycling to the freeze exchanger 110 by means of conduit 150.

The described method of ice building can continue as long as desired, but generally will proceed until the ice storage tank is about one-half to three-fourths full of ice with the balance a liquid water phase.

When it is desired to utilize the cooling capacity stored in the form of ice for cooling purposes, cold water can be withdrawn from ice storage tank 140 by conduit 158 and fed to pump 160. Pump 160 delivers the cold water to conduit 162 which feeds it to heat exchanger 164 to indirectly cool a warm fluid fed thereto by conduit 166 and withdrawn through conduit 168 as cold fluid. This results in the water becoming warm. The warm water is withdrawn from heat exchanger 164 through conduit 170 and is fed into the top or upper interior portion of ice storage tank 140. As the warm water flows through the ice it is cooled by transfer of heat to the ice, thereby causing the ice to melt. This system can continue to operate so long as ice is available in the ice storage tank. Desirably, the amount of ice in the tank available for cooling should be adequate for the intended cooling period.

The apparatus described in conjunction with FIG. 2 is a closed system in which a predetermined volume or mass of water containing a dissolved mineral content is substantially or essentially all maintained in the storage tank. The entire volume of water, however, can be liquid or a mixture of ice and a liquid water phase with the fraction of ice varying from near zero up to a practical maximum of about 70% by weight or above of the water in the form of ice. Since the tank is fully enclosed and insulated a visual determination of the amount of ice in the tank is not practical, even through the tank top, because the ice floats above a layer of a liquid water phase which cannot be seen through the floating ice.

Since it is important to determine the amount of ice, and also the amount of liquid phase water in the tank, so as to have enough ice available to meet cooling load requirements, periodic electrical conductivity measurements are made of the water layer at the bottom of the tank. Water is withdrawn from the water layer at the bottom of tank 140 by means of conduit 180 and pump 182 and fed to conduit 184 which feeds it through electrical conductivity meter 186. The water exits the conductivity meter 186 to conduit 188 which returns it to the top interior of tank 140. As the quantity of ice in tank 140 increases the electrical conductivity of the water beneath the ice will increase almost linearly therewith due to the increase in the dissolved mineral content of the liquid water phase. This comes about naturally because the ice crystals form from pure water and exclude the minerals as they develop. By taking periodic or continuous measurements of the liquid phase water electrical conductivity, and comparing those measurements with the electrical conductivity of the water when it is present in the tank without any ice present, the amount of ice in the tank can be determined.

Figure 3:
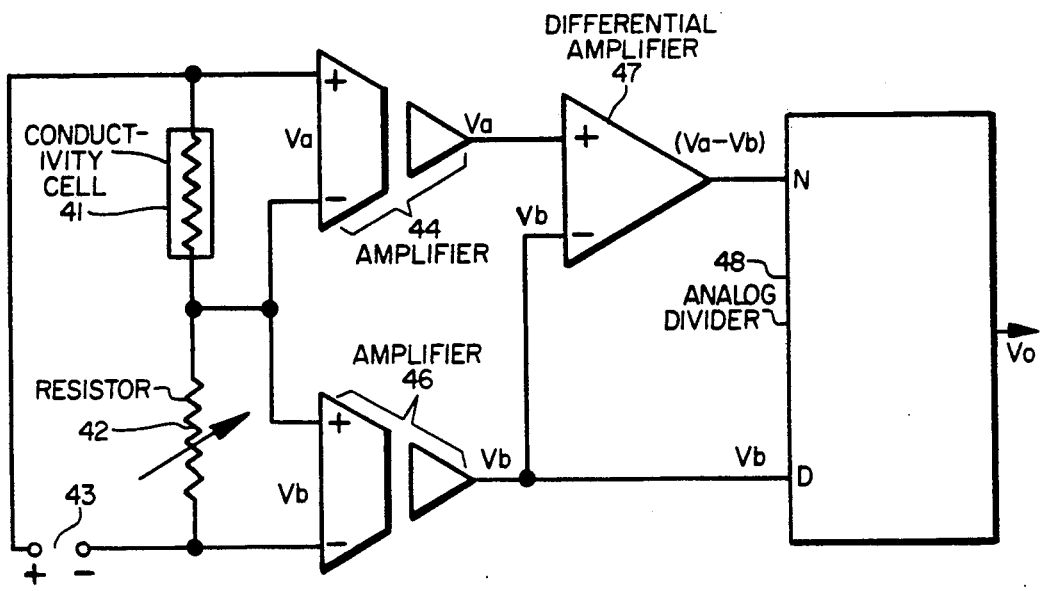
FIG. 3 is a schematic diagram of an instrument embodying the method of the invention which can be used for measuring the fraction of ice produced by freezing an aqueous liquid.

A schematic diagram of an instrument for measuring the fraction of ice in an ice slurry, in accordance with the method of the invention, is shown in FIG. 3. A conductivity cell 41, in which the conductivity of the liquid water in an ice slurry is measured, is depicted as an active resistive element which is connected in series with an adjustable resistance 42 across a constant voltage power supply 43. The voltage drop across the conductivity cell 41, designated $V_a$, is inversely proportional to the conductivity of an ice slurry sample in cell 41.

Before use of the instrument shown in FIG. 3, an initial adjustment is made by circulating the unfrozen water, i.e., before any ice is made, through the conductivity cell 41 and adjusting variable resistor 42 such that the voltage drop $V_b$ across resistor 42 is equal to $V_a$, i.e., the quantity $(V_a - V_b)$ becomes equal to 0. Thereafter, the fraction of ice in an ice slurry measured in the conductivity cell 41 can be expressed as follows:

$$I/M = 1 - (V_a/V_b) \tag{5}$$
$$= (V_b - V_a)/V_b \tag{6}$$

The voltages $V_a$ and $V_b$ are passed through individual amplifiers 44 and 46, which are preferably isolation amplifiers, and fed into the input of a unity gain differential amplifier 47. The output of amplifier 47 is a voltage equal to the quantity $(V_a - V_b)$. This difference voltage and $V_b$ are supplied to an analog divider 48 having an output voltage $V_o$ representing a fraction in which $(V_a - V_b)$ is the numerator and $V_b$ is the denominator, i.e., $$V_o = (V_a - V_b) / V_b \tag{7}$$

Equation (7) is identical to equation (6) except for a difference in sign which is immaterial in practice. The absolute value of $V_o$ is thus representative of the ice fraction in a slurry under test.

By using amplifiers having unity gain throughout, $V_o$ can be read directly as an ice fraction. For example, a reading $V_o$ of 0.45 volts represents an ice fraction of 0.45 or about 45% by weight of ice in the slurry sample in conductivity cell 41.

Figure 4:
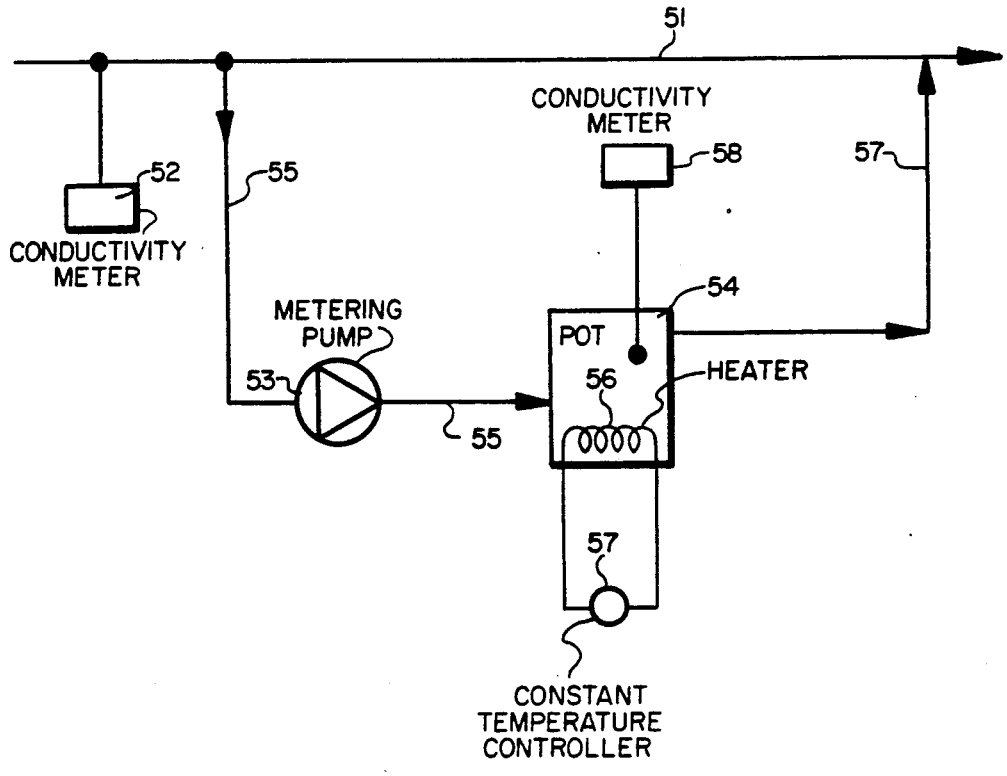
FIG. 4 is a schematic diagram of apparatus for measuring the ice fraction in a slurry continuously flowing through a conduit.

FIG. 4 represents a system for continuously measuring the fraction of ice in an ice slurry moving in conduit 51. The conductivity of the liquid fraction in the ice slurry is measured by a conventional conductivity meter 52. A side stream constituting a representative sample of the liquid and ice in the slurry passing through conduit 51 is diverted to branch conduit 55 containing metering pump 53 and fed to pot 54 provided with a heater 56 energized by a constant temperature controller 57 and provided with a conductivity meter 58. Within the pot, the slurry sample is sufficiently heated by heater 56 to melt all of the ice therein, with the resulting conductivity of the water being measured by meter 58. The sample exiting from pot 54 may be returned through conduit 57 to the main ice slurry flow conduit 51 or the sample may be discarded. The difference in conductivity as measured by meters 52 and 58 can be used to determine the fraction of ice in the slurry passing through conduit 51 in accordance with equation (4).

It will be evident to those skilled in the art that the conductivity signals measured in the systems shown in FIGS. 1 to 4 can be fed to an appropriately programmed computer or microprocessor which can calculate and record or display the fractions of ice in the slurries under test on a continuous basis.

The foregoing detailed description has been given for clearness of understanding only, and no unnecessary limitations should be understood therefrom, as modifications will be obvious to those skilled in the art.

What is claimed is:

1. A method comprising:
   determining the electrical conductivity of water containing a measured concentration of dissolved minerals;

cooling at least some of the water to form ice in liquid phase water;

measuring the increase in the electrical conductivity of the liquid water phase due to the increase in the mineral content thereof as a result of the natural exclusion of minerals from the ice; and correlating the measured electrical conductivity of the water to the liquid water phase not converted to ice to determine the amount of ice which has been produced.

2. A method according to claim 1 in which the water, before any portion thereof is frozen to ice, has a maximum dissolved mineral content of about 2000 ppm.

3. A method comprising:

isolating a mass of water containing a measured concentration of dissolved minerals;

determining the electrical conductively of the undiluted unconcentrated water;

cooling increasing amounts of the mass of water to form ice, in a progressively increasing amount, in liquid water phase;

measuring the increase in the electrical conductivity of the cool water due to the progressive increase in the mineral content of the liquid water phase as a result of the natural exclusion of minerals from the ice; and correlating the measured electrical conductivity of the water before any of the water is converted to ice, to the electrical conductivity of the liquid water phase not converted to ice to determine the amount of ice which has been produced.

4. A method of determining the amount of ice slurry in an ice storage tank which comprises:

firstly determining the electrical conductivity of water containing a measured amount of dissolved minerals;

feeding a volume of the water, some of which may be in the form of ice, to an ice storage tank;

cooling increasing amounts of the tank water to form more ice and storing the additional ice in the tank;

secondly determining the increase in the electrical conductivity of the liquid water phase in the tank due to the natural progressive increase in the mineral content of the water as the amount of water in liquid phase decreases and the amount of ice increases; and by means of the difference between the first and second electrical conductivities determining the portions of ice and water in liquid phase in the tank.

5. A method according to claim 4 in which the ice is formed outside of the tank using water withdrawn from the water volume in the tank and the ice admixed with water is fed to the tank interior.

6. A method of determining the portions of ice and water in a storage tank;

the ice in the storage tank being produced by freezing a portion of a known volume of water having a dissolved mineral content of measured amount when the water is entirely in the liquid phase;

the volume of water in liquid phase, before any ice is produced from it, having an initial electrical conductivity;

the tank also containing essentially all of the remaining portion of the volume of water in liquid phase;

said ice portion being formed with essentially all of the dissolved mineral content being excluded from the ice and remaining dissolved in the liquid water phase portion; and measuring the electrical conductivity of the remaining portion of the volume of water in liquid phase and comparing its measured electrical conductivity with the measured electrical conductivity of the water volume before any of the water volume is converted to ice and by means of the difference between the two electrical conductivities determining the portions of ice and water in liquid phase in the tank.

7. A method according to claim 6 in which the ice is formed in the storage tank.

8. A method comprising:

(a) measuring the electrical conductivity $C_i$ of water at a temperature above its freezing point;

(b) cooling the water to produce a mixture of an ice phase and a liquid water phase;

(c) measuring the electrical conductivity $C_n$ of said liquid water phase; and (d) computing the fraction of ice in said mixture by use of the equation $$F = 1 - C_i/C_n$$

wherein F is the fraction of ice in the mixture, $C_i$ is the conductivity of said water before ice formation therein, and $C_n$ is the conductivity of said liquid water phase in a mixture having the ice fraction F.

9. A method for measuring the amount of ice in an ice slurry comprising a mixture of ice and a liquid water phase containing dissolved minerals comprising:

(a) measuring the electrical conductivity of the liquid water phase of the ice slurry;

(b) isolating a representative sample of the ice slurry;

(c) heating the ice slurry sample to melt all of the ice therein;

(d) measuring the electrical conductivity of the melted ice slurry sample; and (e) calculating the ice fraction by use of the equation:

$$F = 1 - C_i/C_n$$

wherein F is the fraction of ice in the ice slurry, $C_i$ is the conductivity of the melted ice slurry sample, and $C_n$ is the conductivity of said liquid water phase of the ice slurry having the ice fraction F.

10. A method for continuous measurement of an ice fraction in an ice slurry, comprising a mixture of ice and a liquid water phase containing dissolved minerals, passing a given point, said method comprising the steps of:

(a) measuring the conductivity $C_n$ of the liquid water phase of the ice slurry at said point;

(b) isolating a representative sample of the ice slurry;

(c) heating the ice slurry sample sufficiently to melt all of the ice therein;

(d) measuring the conductivity $C_i$ of the melted ice slurry sample; and (e) calculating the ice fraction by use of the equation $$F = 1 - C_i/C_n$$

wherein F is the fraction of ice in the ice slurry, $C_i$ is the conductivity of the melted ice slurry sample, and $C_n$ is the conductivity of said liquid water phase of the ice slurry having the ice fraction F.

11. Apparatus comprising:

a storage tank adapted to contain a volume of water, having a dissolved mineral content, which can be cooled and converted to ice;

a conduit communicating with the bottom interior of the tank for withdrawing water in liquid phase from the tank and returning it to the tank; and means for measuring the electrical conductivity of the liquid water phase flowing through said conduit to thereby determine the amount of ice, if any, in the tank.

12. Apparatus comprising:

a main conduit through which an ice slurry produced by cooling water having a dissolved mineral content to form an ice phase and a liquid water phase can flow;

means to measure the electrical conductivity of the liquid water phase content of the ice slurry in the main conduit;

a branch conduit communicating with the main conduit for withdrawing an ice slurry sample therefrom and delivering it to a pot;

heater means associated with the pot to melt the ice in the sample and produce a totally liquid water phase sample; and means to measure the electrical conductivity of the totally liquid water phase sample in the pot.

13. Apparatus according to claim 12 in which a constant temperature controller is associated with the pot to maintain the totally liquid water phase sample at a temperature slightly above freezing.

14. Apparatus according to claim 12 in which a conduit communicates with the pot for withdrawing the totally liquid water phase sample from the pot and returning it to the main conduit for addition to ice slurry flowing therein.

15. Apparatus for measuring the fraction of ice in a slurry produced by freezing water comprising:

a conductivity cell for measuring the conductivity of water, said cell being connected in series with a variable resistor across a source of constant voltage;

a first amplifier receiving at its input a first signal representing the voltage drop across said conductivity cell and producing an output signal $V_a$ representing said first signal;

a second amplifier receiving at its input a second signal representing the voltage drop across said variable resistor and producing an output signal $V_b$ representing said second signal;

a differential amplifier having two inputs, to one of which said signal $V_a$ is applied and to the other of which said signal $V_b$ is applied, the amplifier producing an output signal representing the difference $(V_a - V_b)$ between said input signals; and an analog divider having a first input to which said signal $(V_a - V_b)$ is applied, and a second input to which said signal $V_b$ is applied, said divider producing an output signal $V_o$ representing the fraction $$\frac{V_a - V_b}{V_b}$$

and $V_o$ also representing the fraction of ice in an ice slurry introduced into said conductivity cell.

16. The apparatus of claim 15 wherein all of said amplifiers have unity gain.

17. The apparatus of claim 15 wherein said first and second amplifiers are isolation amplifiers.

18. A method of determining the amount of ice slurry in an ice storage tank which comprises:

positioning a volume of water containing a measured amount of dissolved minerals in an ice storage tank, with the water having a predetermined electrical conductivity;

cooling increasing amounts of the tank water to form ice in the storage tank and storing the ice in the tank;

determining the increase in the electrical conductivity of the liquid water phase in the tank due to the natural progressive increase in the mineral content of the water as the amount of water in liquid phase decreases and the amount of ice increases; and by means of the difference between the first and second electrical conductivities determining the portions of ice and water in liquid phase in the tank.

19. A method of determining the portions of ice and water in a storage tank;

positioning a known volume of water, having a dissolved mineral content of measured amount when the water is entirely in the liquid phase, in a storage tank;

the volume of water in liquid phase, before any ice is produced from it, having an initial electrical conductivity;

withdrawing water from the tank and forming ice from the water outside of the tank and then feeding the ice admixed with said water to the tank interior;

the tank also containing essentially all of the remaining portion of the volume of water in liquid phase;

said ice portion being formed with essentially all of the dissolved mineral content being excluded from the ice and remaining dissolved in the liquid water phase portion; and measuring the electrical conductivity of the remaining portion of the volume of water in liquid phase and comparing its measured electrical conductivity with the measured electrical conductivity of the water volume before any of the water volume is converted to ice and by means of the difference between the two electrical conductivities determining the portions of ice and water in liquid phase in the tank.

* * * * *